US012678545B2

(12) United States Patent
Mizuno et al.

(10) Patent No.: US 12,678,545 B2
(45) Date of Patent: Jul. 14, 2026

(54) DIALYSIS SYSTEM AND DIALYSIS SYSTEM OPERATION METHOD

(71) Applicant: HAMAMATSU PHOTONICS K.K., Hamamatsu (JP)

(72) Inventors: Toshihiko Mizuno, Hamamatsu (JP); Takashi Watanabe, Hamamatsu (JP)

(73) Assignee: HAMAMATSU PHOTONICS K.K., Hamamatsu (JP)

( * ) Notice: Subject to any disclaimer, the term of this patent is extended or adjusted under 35 U.S.C. 154(b) by 731 days.

(21) Appl. No.: 17/912,963

(22) PCT Filed: Feb. 2, 2021

(86) PCT No.: PCT/JP2021/003766

§ 371 (c)(1),
(2) Date: Sep. 20, 2022

(87) PCT Pub. No.: WO2021/199655

PCT Pub. Date: Oct. 7, 2021

(65) Prior Publication Data

US 2023/0112737 A1    Apr. 13, 2023

(30) Foreign Application Priority Data

Mar. 31, 2020    (JP) ................................ 2020-063656

(51) Int. Cl.
A61M 1/14        (2006.01)
A61M 1/36        (2006.01)
(52) U.S. Cl.
CPC ................ *A61M 1/14* (2013.01); *A61M 1/36* (2013.01)

(58) Field of Classification Search
CPC .................................. A61M 1/14; A61M 1/36
See application file for complete search history.

(56) References Cited

U.S. PATENT DOCUMENTS 9,440,017 B2 *   9/2016   Rohde ................. A61M 1/3616
2002/0085951 A1    7/2002   Gelfand et al.
2009/0275808 A1 *  11/2009   DiMaio .................... A61B 6/56
                                                128/845

FOREIGN PATENT DOCUMENTS

CN      108135505 A      6/2018
CN      108143426 A      6/2018
CN      109009064 A     12/2018
CN      109260536 A      1/2019
        (Continued)

OTHER PUBLICATIONS

JP-2012040058-A_English translation (Year: 2012).*
        (Continued)

*Primary Examiner* — Youngsul Jeong
(74) *Attorney, Agent, or Firm* — FAEGRE DRINKER BIDDLE & REATH LLP

(57)                    ABSTRACT

A dialysis system includes a dialysis apparatus, a measurement apparatus, and a control apparatus. The dialysis apparatus performs hemodialysis on a dialysis subject. The measurement apparatus measures a cerebral regional oxygen saturation of the dialysis subject. The control apparatus adjusts a hemodialysis operating condition by the dialysis apparatus so as to suppress decrease in the cerebral rSO2 based on the cerebral rSO2 of the dialysis subject measured by the measurement apparatus during operation of the hemodialysis by the dialysis apparatus.

9 Claims, 3 Drawing Sheets

(56)          References Cited

FOREIGN PATENT DOCUMENTS

| | | | | | |
|---|---|---|---|---|---|
| DE | 10047421 | C1 | | 1/2003 | |
| EP | 1810703 | A1 | | 7/2007 | |
| JP | 2012040058 | A | * | 3/2012 | ............. G01N 21/85 |
| JP | 2014117503 | A | * | 6/2014 | ......... A61B 5/14551 |
| JP | 2020-018742 | A | | 2/2020 | |

OTHER PUBLICATIONS

JP-2014117503-A_English translation (Year: 2014).*
International Preliminary Report on Patentability mailed Oct. 13, 2022 for PCT/JP2021/003766.
Xie Lin, Ren Wanjun, "Impact of Different Dialysis Modalities on the Prognosis of Patients with Cerebral Hemorrhage", Mar. 20, 2015, p. 126-p. 127, including English-language translation.
Editorial Board, "Diagnosis and Treatment of Common Clinical Liver and Kidney Diseases", Jun. 30, 2003, p. 302-p. 304, including English-language translation.

* cited by examiner

DIALYSIS SYSTEM AND DIALYSIS SYSTEM OPERATION METHOD

TECHNICAL FIELD

The present disclosure relates to a dialysis system and a dialysis system operation method.

BACKGROUND ART

Hemodialysis, which artificially replaces a renal function for a person whose renal function is deteriorated, removes unnecessary or harmful substances from blood of a dialysis subject, and performs water removal or fluid replacement on the blood of the dialysis subject. A blood pressure of the dialysis subject may be lowered due to the water removal during the hemodialysis operation. Lowering of the blood pressure leads to reduction of a cerebral blood flow. The dialysis subject shows symptoms of malaise and yawn due to reduction of the cerebral blood flow, and shows various symptoms such as nausea, vomiting, and decreased level of consciousness when the cerebral blood flow is further reduced. Further, reduction of the cerebral blood flow during the hemodialysis operation is considered to be related to vascular dementia and cerebrovascular disease.

Patent Document 1 discloses an invention in which the blood pressure of the dialysis subject is monitored during the hemodialysis operation, and abnormality is informed or the like when the blood pressure is lowered. According to this invention, when the blood pressure of the dialysis subject is lowered during the hemodialysis operation, a doctor or the like may suppress occurrence of symptoms described above due to cerebral blood flow reduction by adjusting a hemodialysis operating condition.

CITATION LIST

Patent Literature

Patent Document 1: Japanese Patent Application Laid-Open Publication No. 2020-018742

SUMMARY OF INVENTION

Technical Problem

The blood pressure cannot be measured continuously and can only be measured intermittently. On the other hand, a state of the dialysis subject during the hemodialysis operation may suddenly change. Therefore, by adjusting the hemodialysis operating condition when the blood pressure measured value of the dialysis subject is lowered, it may not be in time to suppress occurrence of symptoms due to cerebral blood flow reduction. Further, it is said that, when the dialysis subject suffers from diabetes, symptoms due to cerebral blood flow reduction may occur even when the blood pressure measured value is within the normal range.

An object of an embodiment is to provide a dialysis system and a dialysis system operation method capable of more reliably suppressing occurrence of symptoms due to cerebral blood flow reduction during hemodialysis operation.

Solution to Problem

An embodiment is a dialysis system. The dialysis system includes (1) a dialysis apparatus for performing hemodialysis on a dialysis subject; (2) a measurement apparatus for measuring a regional oxygen saturation of the dialysis subject; and (3) a control apparatus for adjusting a hemodialysis operating condition by the dialysis apparatus so as to suppress decrease in the regional oxygen saturation based on the regional oxygen saturation measured by the measurement apparatus during operation of the hemodialysis by the dialysis apparatus.

An embodiment is a dialysis system operation method. The dialysis system operation method is a method for operating a dialysis system including a dialysis apparatus for performing hemodialysis on a dialysis subject; and a measurement apparatus for measuring a regional oxygen saturation of the dialysis subject, and includes adjusting a hemodialysis operating condition by the dialysis apparatus so as to suppress decrease in the regional oxygen saturation based on the regional oxygen saturation measured by the measurement apparatus during operation of the hemodialysis by the dialysis apparatus.

Advantageous Effects of Invention

According to the dialysis system and the dialysis system operation method of the embodiments, it is possible to more reliably suppress occurrence of symptoms due to cerebral blood flow reduction during hemodialysis operation.

DESCRIPTION OF EMBODIMENTS

Hereinafter, embodiments of a dialysis system and a dialysis system operation method will be described in detail with reference to the accompanying drawings. In the description of the drawings, the same elements will be denoted by the same reference signs, and redundant description will be omitted. The present invention is not limited to these examples.

Figure 1:
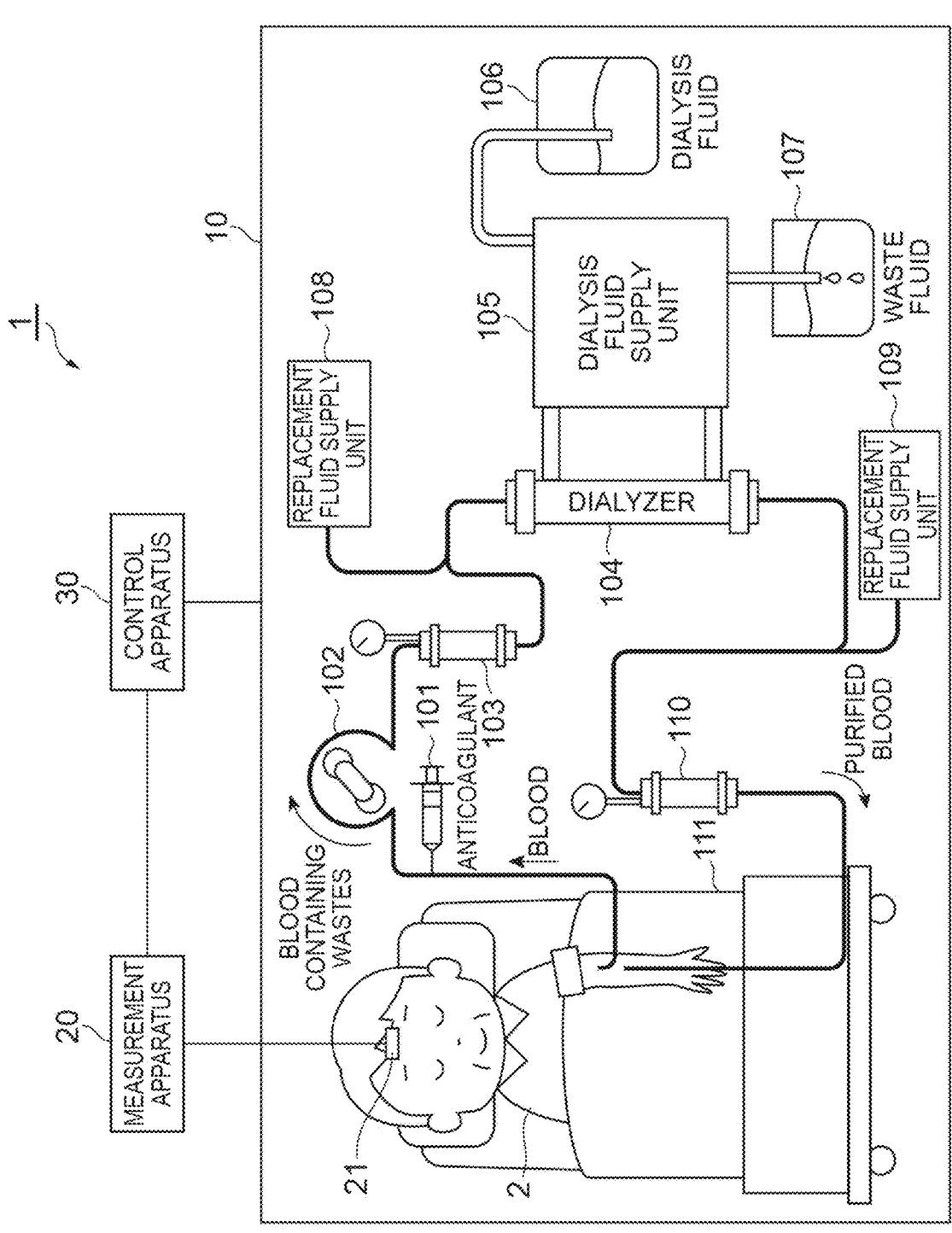
FIG. 1 is a diagram illustrating a configuration of a dialysis system 1.

FIG. 1 is a diagram illustrating a configuration of a dialysis system 1. The dialysis system 1 includes a dialysis apparatus 10, a measurement apparatus 20, and a control apparatus 30.

The dialysis apparatus 10 performs hemodialysis on a dialysis subject 2. The dialysis apparatus 10 includes an anticoagulant supply unit 101, a pump 102, a pressure gauge 103, a dialyzer 104, a dialysis fluid supply unit 105, a dialysis fluid container 106, a waste fluid container 107, a replacement fluid supply unit 108, a replacement fluid supply unit 109, a pressure gauge 110, and tubes for flowing blood, dialysis fluid, replacement fluid, and the like therebetween. Further, the dialysis apparatus 10 includes a placing stage 111 for placing a head or a leg of the dialysis subject 2.

The anticoagulant supply unit 101 supplies an anticoagulant for suppressing coagulation of blood taken from a body of the dialysis subject 2 to the inside of a tube through which the blood flows. The pump 102 controls the flow of the blood in the tube to draw the blood from the body of the dialysis subject 2. The pump 102 can adjust a blood flow rate. The pressure gauge 103 measures a pressure of the blood inside the tube between the pump 102 and the dialyzer 104.

The dialyzer 104 performs water removal and removes unnecessary or harmful substances from the blood using a dialysis fluid supplied from the dialysis fluid supply unit 105. The dialysis fluid supply unit 105 supplies the dialysis fluid contained in the dialysis fluid container 106 to the dialyzer 104, and outputs the substances and the like removed by the dialyzer 104 and the used dialysis fluid to the waste fluid container 107.

The dialysis fluid supply unit 105 can adjust a dialysis fluid supply amount to the dialyzer 104 (that is, a dialysis fluid flow rate in the dialyzer 104). The dialysis fluid supply unit 105 or the dialysis fluid container 106 can adjust a temperature of the dialysis fluid supplied to the dialyzer 104, or the dialyzer 104 can adjust the temperature of the dialysis fluid in the dialyzer 104. Further, the dialyzer 104 can adjust a water removal amount.

The replacement fluid supply unit 108 performs fluid replacement on the blood before being input to the dialyzer 104. The replacement fluid supply unit 109 performs fluid replacement on the purified blood after being output from the dialyzer 104. The fluid is saline and may contain medical agent such as glucose liquid. The replacement fluid supply unit 108 and the replacement fluid supply unit 109 can adjust an amount or timing of the fluid replacement. Both of the replacement fluid supply unit 108 and the replacement fluid supply unit 109 may be provided, or only one of them may be provided. The pressure gauge 110 measures a pressure of the purified blood being returned to the dialysis subject 2.

The placing stage 111 for placing a head or a leg of the dialysis subject 2 may be a bed, or may be a chair. When the placing stage 111 is the bed, the placing stage 111 has a mechanism for adjusting a height of a portion corresponding to the head of the dialysis subject 2, and a mechanism for adjusting a height of a portion corresponding to the leg of the dialysis subject 2.

When the placing stage 111 is the chair, the placing stage 111 can adjust a height of the head of the dialysis subject 2 by having a mechanism for adjusting an inclination of a backrest of the chair, and further, can adjust a height of the leg of the dialysis subject 2 by having a mechanism for adjusting a height of a leg rest provided at a front lower part of the chair.

The measurement apparatus 20 measures a regional oxygen saturation of the dialysis subject 2. Preferably, the measurement apparatus 20 measures a cerebral regional oxygen saturation of the dialysis subject 2. The regional oxygen saturation (regional saturation of oxygen, rSO2) indicates a ratio of oxygenated hemoglobin in total hemoglobin. There is a good correlation between the cerebral rSO2 and a cerebral blood flow.

The measurement apparatus 20 is used together with a probe 21 provided on a forehead of the dialysis subject 2, and can measure the cerebral rSO2 of the dialysis subject 2 by near infrared spectroscopy (NIRS).

Figure 2:
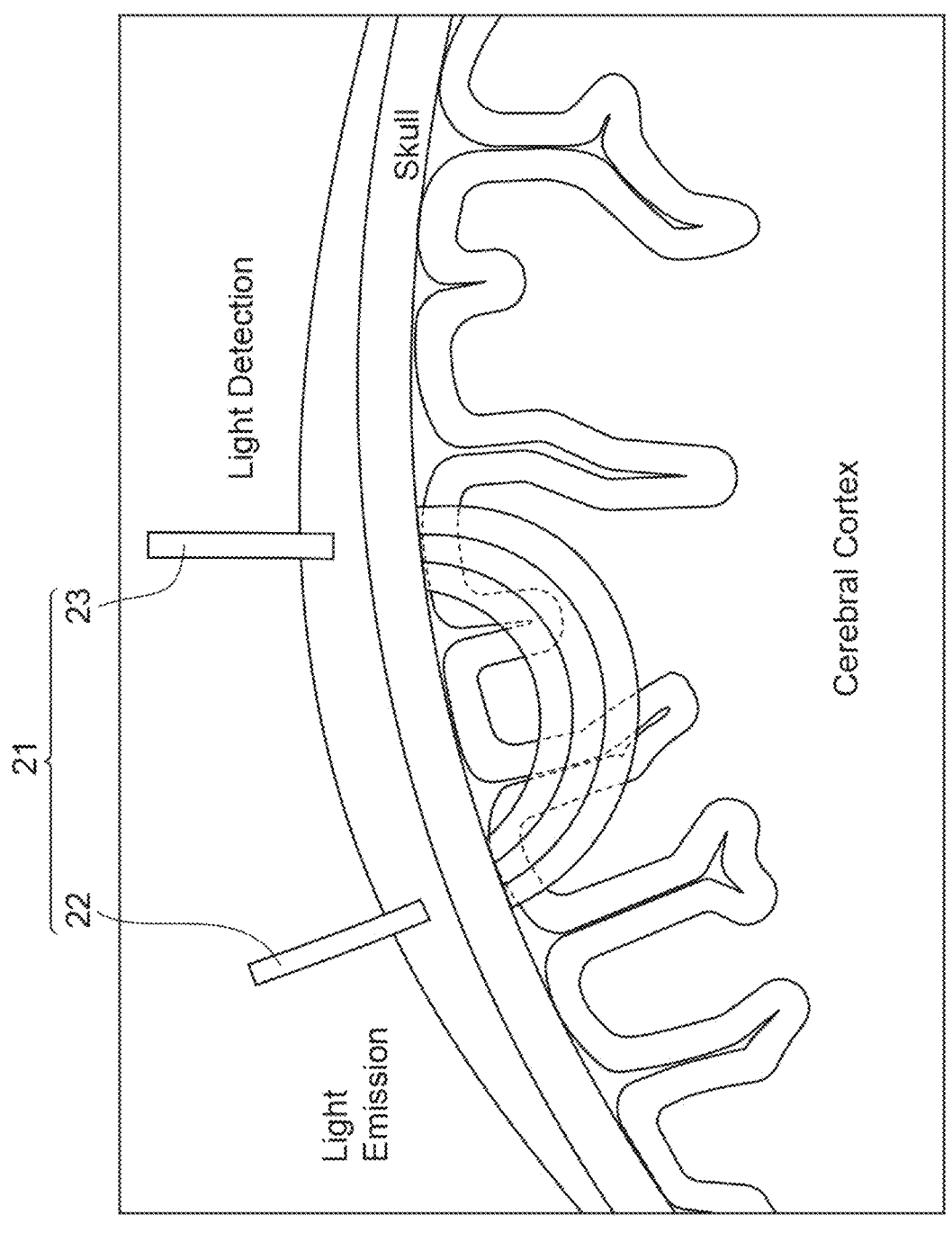
FIG. 2 is a diagram illustrating a probe 21 of a measurement apparatus 20.

As illustrated in FIG. 2, the probe 21 includes an emission unit 22 and a detection unit 23 which are spaced apart from each other by a predetermined distance. Near-infrared light (preferably, near-infrared light having a plurality of central wavelengths) is applied from the emission unit 22 to the forehead of the dialysis subject 2, and the near-infrared light after being scattered and absorbed in the brain of the dialysis subject 2 is detected by the detection unit 23. The cerebral rSO2 of the dialysis subject 2 can be measured based on detection results by the detection unit 23.

It is preferable that the probe 21 includes a plurality of detection units, and the measurement apparatus 20 measures the cerebral rSO2 in each of a plurality of portions of the forehead of the dialysis subject 2. In this case, any one of the cerebral rSO2 measured values of the plurality of portions may be used, or an average value thereof may be used. Further, when any measured value out of the cerebral rSO2 measured values of the plurality of portions is determined to be abnormal, the abnormal value may be excluded and another measured value may be used.

The measurement apparatus 20 can measure the cerebral rSO2 of the dialysis subject 2 non-invasively and continuously (or at very short time intervals). A measurement apparatus capable of measuring the cerebral rSO2 is sold as a product by Hamamatsu Photonics K.K. or the like.

The control apparatus 30 adjusts a hemodialysis operating condition by the dialysis apparatus 10 so as to suppress decrease in the cerebral rSO2 based on the cerebral rSO2 of the dialysis subject 2 measured by the measurement apparatus 20 during operation of the hemodialysis by the dialysis apparatus 10. The control apparatus 30 includes an operation unit, a storage unit, an input unit, an output unit, and the like, and may be constituted by a computer, a tablet, or the like.

The control apparatus 30 inputs the cerebral rSO2 measured value obtained by the measurement apparatus 20 in real time. Since the cerebral rSO2 measured value may vary with time due to noise superimposition or the like, it is preferable that the control apparatus 30 take a moving average for smoothing time-series data of the cerebral rSO2 measured value. In this case, a time width for the moving average may be, for example, about several seconds to several tens of seconds.

The control apparatus 30 monitors a temporal change of the cerebral rSO2 measured value. Further, when the degree of decrease of the cerebral rSO2 measured value satisfies a predetermined condition, the control apparatus 30 adjusts the hemodialysis operating condition by the dialysis apparatus 10 to suppress decrease in the cerebral rSO2.

The control apparatus 30 may adjust the hemodialysis operating condition by the dialysis apparatus 10 so as to suppress decrease in the cerebral rSO2 when a decrease ratio $((A_1 - A_0)/A_0)$ of the cerebral rSO2 measured value $A_1$ during the operation of the hemodialysis by the dialysis apparatus 10 becomes larger than a threshold value (for example, about 15% to 20%) with respect to the cerebral rSO2 measured value $A_0$ before the operation of the hemodialysis by the dialysis apparatus 10.

Further, the control apparatus 30 may adjust the hemodialysis operating condition by the dialysis apparatus 10 so as to suppress decrease in the cerebral rSO2 when a decreasing rate of the cerebral rSO2 measured value during the operation of the hemodialysis by the dialysis apparatus 10 becomes larger than a threshold value (for example, when the decrease ratio in 30 seconds becomes larger than 10%).

The adjustment of the hemodialysis operating condition by the dialysis apparatus 10 for suppressing the decrease in the cerebral rSO2 of the dialysis subject 2 is preferably as follows.

The control apparatus 30 may adjust a blood flow rate in the dialysis apparatus 10 so as to suppress the decrease in the cerebral rSO2 of the dialysis subject 2. Specifically, the blood flow rate is decreased by the pump 102 to decrease an amount of the blood taken from the dialysis subject 2.

The control apparatus 30 may adjust a dialysis fluid flow rate in the dialysis apparatus 10 so as to suppress the decrease in the cerebral rSO2 of the dialysis subject 2.

Specifically, the dialysis fluid flow rate is decreased by the dialysis fluid supply unit 105.

The control apparatus 30 may adjust a temperature of the dialysis fluid in the dialysis apparatus 10 so as to suppress the decrease in the cerebral rSO2 of the dialysis subject 2. Specifically, the dialysis fluid is set to a temperature (for example, about 34° C. to 35° C.) lower than a body temperature of the dialysis subject 2 by the dialyzer 104, the dialysis fluid supply unit 105, or the dialysis fluid container 106, and the low-temperature purified blood is returned to the dialysis subject 2, thereby constricting the blood vessel of the dialysis subject 2.

The control apparatus 30 may adjust a water removal amount in the dialysis apparatus 10 so as to suppress the decrease in the cerebral rSO2 of the dialysis subject 2. Specifically, the amount of water removal by the dialyzer 104 is decreased.

The control apparatus 30 may adjust an amount or timing of fluid replacement in the dialysis apparatus 10 so as to suppress the decrease in the cerebral rSO2 of the dialysis subject 2. Specifically, the amount of fluid replacement by the replacement fluid supply unit 108 or the replacement fluid supply unit 109 is increased or the timing is delayed.

The control apparatus 30 may adjust a height of the placing stage 111 for placing the head or the leg of the dialysis subject in the dialysis apparatus 10 so as to suppress the decrease in the cerebral rSO2 of the dialysis subject 2.

Specifically, when the placing stage 111 is a bed, a position corresponding to the head of the dialysis subject 2 is lowered or a position corresponding to the leg of the dialysis subject 2 is raised. When the placing stage 111 is a chair, the head of the dialysis subject 2 is lowered by tilting a backrest of the chair backward, or the leg of the dialysis subject 2 is raised by raising a leg rest provided at a front lower part of the chair.

By adjusting any of the above hemodialysis operating conditions, reduction of a cerebral blood flow of the dialysis subject 2 can be suppressed, and the decrease of the cerebral rSO2 of the dialysis subject 2 can be suppressed.

In addition, suppression of the cerebral blood flow reduction includes not only decreasing a reduction rate of the cerebral blood flow but also turning the cerebral blood flow upward. Further, suppression of the decrease in the cerebral rSO2 includes not only decreasing a decreasing rate of the cerebral rSO2 but also turning the cerebral rSO2 upward. The control apparatus 30 may combine the adjustments of the hemodialysis operating conditions described above, or may stop the hemodialysis operation by the dialysis apparatus 10.

It is also preferable that the control apparatus 30 has means for informing when it is determined that the hemodialysis operating condition by the dialysis apparatus 10 needs to be adjusted so as to suppress the decrease in the cerebral rSO2 (when the degree of the decrease of the cerebral rSO2 measured value satisfies a predetermined condition).

The above informing means may appeal to the auditory sense by an alarm sound, a message voice, or the like, or may appeal to the visual sense by light emission of a light emitter, message display, or the like. Further, the informing means may inform a person near the dialysis subject 2 or inform a doctor or the like in a room different from the room where the dialysis subject 2 is present by communication via an electric communication line or an optical communication line.

In the operation method of the dialysis system including the dialysis apparatus 10 and the measurement apparatus 20, the doctor or the like receiving the above information can adjust the hemodialysis operating condition by the dialysis apparatus 10 so as to suppress the decrease in the cerebral rSO2 based on the cerebral rSO2 of the dialysis subject 2 measured by the measurement apparatus 20 during the operation of the hemodialysis by the dialysis apparatus 10. When the doctor or the like adjusts the hemodialysis operating condition by the dialysis apparatus 10, the control apparatus 30 of the dialysis system does not need to automatically adjust the hemodialysis operating condition described above.

Figure 3:
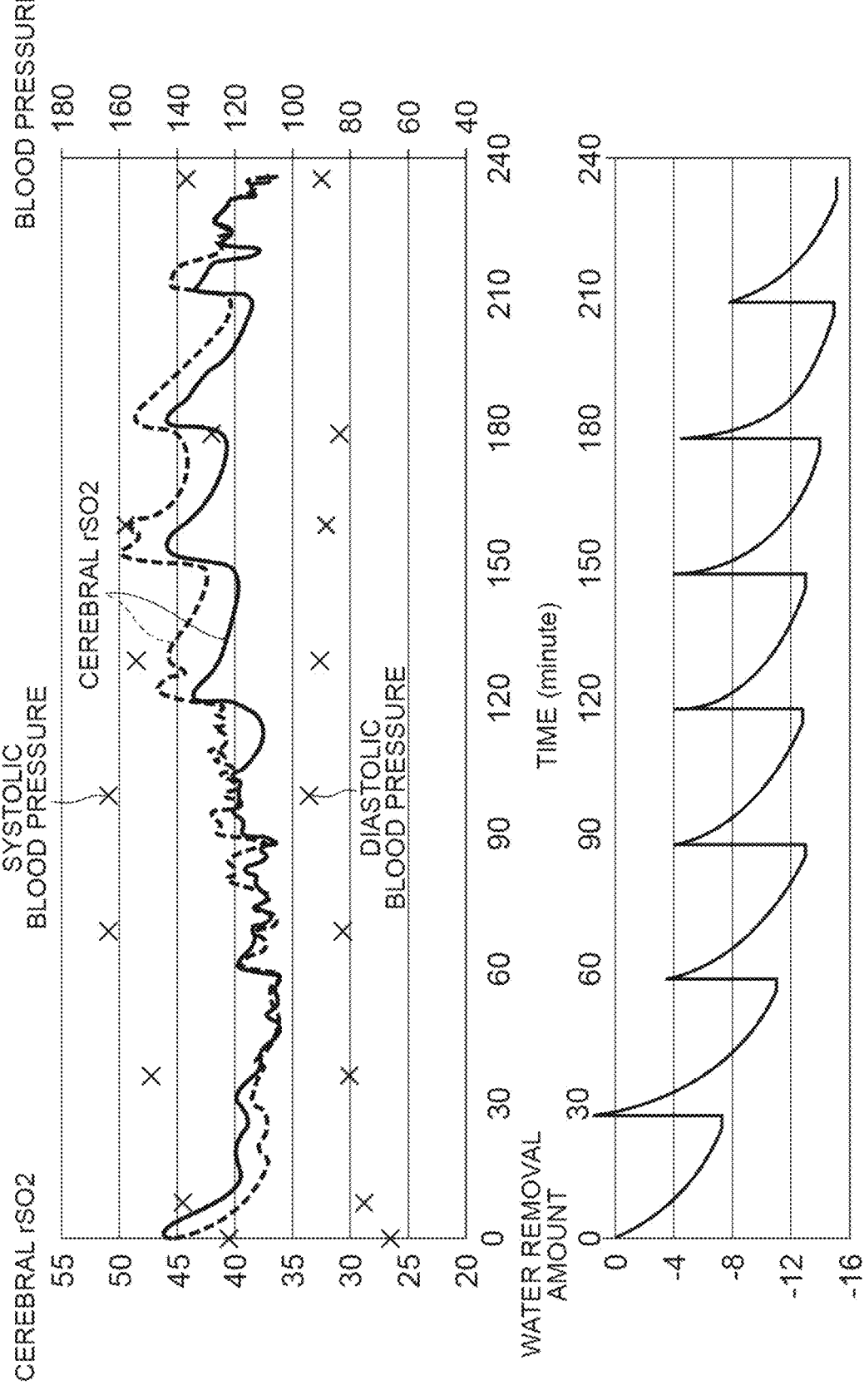
FIG. 3 is a diagram showing temporal changes of a cerebral rSO2 measured value, a blood pressure measured value, and a water removal amount during hemodialysis operation.

FIG. 3 is a diagram showing temporal changes of a cerebral rSO2 measured value, a blood pressure measured value, and a water removal amount during the hemodialysis operation. Graphs of the cerebral rSO2 indicate the measured values respectively in the two portions of the forehead of the dialysis subject. X-marks indicate measured values of a systolic blood pressure and a diastolic blood pressure of the dialysis subject. The water removal amount indicates an integrated value from the start of the hemodialysis operation. The sudden increase of the integrated value every 30 minutes is caused by the fluid replacement.

As shown in this diagram, the blood pressure measured value is less affected by the water removal or the fluid replacement. On the other hand, the cerebral rSO2 measured value gradually decreases by continuously performing the water removal, and by performing the fluid replacement, the cerebral rSO2 measured value increases. As described above, since the cerebral rSO2 correlated with the cerebral blood flow is sensitively changed by adjusting the water removal amount or the amount or timing of the fluid replacement, occurrence of symptoms due to the cerebral blood flow reduction during the hemodialysis operation can be more reliably suppressed.

Conventionally, in a case where the hemodialysis operating condition is adjusted when the blood pressure of the dialysis subject is lowered during the hemodialysis operation, since the blood pressure can only be measured intermittently, there is a case where it is not in time to suppress occurrence of symptoms due to the cerebral blood flow reduction. Further, it is said that, when the dialysis subject suffers from diabetes, symptoms due to the cerebral blood flow reduction may occur even when the blood pressure measured value is within the normal range.

On the other hand, in the present embodiment, the cerebral rSO2 of the dialysis subject during the hemodialysis operation can be measured continuously, and thus, when the cerebral rSO2 measured value correlated with the cerebral blood flow decreases, the hemodialysis operating condition can be quickly adjusted without waiting for awareness of symptoms of the dialysis subject, and occurrence of symptoms due to the cerebral blood flow reduction during the hemodialysis operation can be more reliably suppressed. Further, even when the dialysis subject suffers from diabetes, since the hemodialysis operating condition can be adjusted based on the cerebral rSO2 measured value correlated with the cerebral blood flow, occurrence of symptoms due to the cerebral blood flow reduction in the hemodialysis operation can be more reliably suppressed.

The dialysis system and the dialysis system operation method are not limited to the embodiments and configuration examples described above, and various modifications are possible.

The dialysis system of the above embodiment includes (1) a dialysis apparatus for performing hemodialysis on a dialysis subject; (2) a measurement apparatus for measuring a regional oxygen saturation of the dialysis subject; and (3) a control apparatus for adjusting a hemodialysis operating condition by the dialysis apparatus so as to suppress decrease in the regional oxygen saturation based on the regional oxygen saturation measured by the measurement apparatus during operation of the hemodialysis by the dialysis apparatus.

In the above dialysis system, the measurement apparatus may measure a cerebral regional oxygen saturation in each of a plurality of portions of a forehead of the dialysis subject as the regional oxygen saturation.

In the above dialysis system, the control apparatus may adjust the hemodialysis operating condition by the dialysis apparatus so as to suppress decrease in the regional oxygen saturation when a decrease ratio of the regional oxygen saturation measured by the measurement apparatus during the operation of the hemodialysis by the dialysis apparatus becomes larger than a threshold value with respect to the regional oxygen saturation measured by the measurement apparatus before the operation of the hemodialysis by the dialysis apparatus.

In the above dialysis system, the control apparatus may adjust the hemodialysis operating condition by the dialysis apparatus so as to suppress decrease in the regional oxygen saturation when a decreasing rate of the regional oxygen saturation measured by the measurement apparatus during the operation of the hemodialysis by the dialysis apparatus becomes larger than a threshold value.

In the above dialysis system, the control apparatus may adjust a blood flow rate in the dialysis apparatus so as to suppress decrease in the regional oxygen saturation. Further, the control apparatus may adjust a dialysis fluid flow rate in the dialysis apparatus so as to suppress decrease in the regional oxygen saturation.

In the above dialysis system, the control apparatus may adjust a temperature of a dialysis fluid in the dialysis apparatus so as to suppress decrease in the regional oxygen saturation. Further, the control apparatus may adjust a water removal amount in the dialysis apparatus so as to suppress decrease in the regional oxygen saturation. Further, the control apparatus may adjust an amount or timing of fluid replacement in the dialysis apparatus so as to suppress decrease in the regional oxygen saturation.

In the above dialysis system, the control apparatus may adjust a height of a placing stage for placing a head or a leg of the dialysis subject in the dialysis apparatus so as to suppress decrease in the regional oxygen saturation.

The dialysis system operation method of the above embodiment is a method for operating a dialysis system including a dialysis apparatus for performing hemodialysis on a dialysis subject; and a measurement apparatus for measuring a regional oxygen saturation of the dialysis subject, and includes adjusting a hemodialysis operating condition by the dialysis apparatus so as to suppress decrease in the regional oxygen saturation based on the regional oxygen saturation measured by the measurement apparatus during operation of the hemodialysis by the dialysis apparatus.

In the above dialysis system operation method, the measurement apparatus may measure a cerebral regional oxygen saturation in each of a plurality of portions of a forehead of the dialysis subject as the regional oxygen saturation.

In the above dialysis system operation method, the hemodialysis operating condition by the dialysis apparatus may be adjusted so as to suppress decrease in the regional oxygen saturation when a decrease ratio of the regional oxygen saturation measured by the measurement apparatus during the operation of the hemodialysis by the dialysis apparatus becomes larger than a threshold value with respect to the regional oxygen saturation measured by the measurement apparatus before the operation of the hemodialysis by the dialysis apparatus.

In the above dialysis system operation method, the hemodialysis operating condition by the dialysis apparatus may be adjusted so as to suppress decrease in the regional oxygen saturation when a decreasing rate of the regional oxygen saturation measured by the measurement apparatus during the operation of the hemodialysis by the dialysis apparatus becomes larger than a threshold value.

In the above dialysis system operation method, a blood flow rate in the dialysis apparatus may be adjusted so as to suppress decrease in the regional oxygen saturation. Further, a dialysis fluid flow rate in the dialysis apparatus may be adjusted so as to suppress decrease in the regional oxygen saturation.

In the above dialysis system operation method, a temperature of a dialysis fluid in the dialysis apparatus may be adjusted so as to suppress decrease in the regional oxygen saturation. Further, a water removal amount in the dialysis apparatus may be adjusted so as to suppress decrease in the regional oxygen saturation. Further, an amount or timing of fluid replacement in the dialysis apparatus may be adjusted so as to suppress decrease in the regional oxygen saturation.

In the above dialysis system operation method, a height of a placing stage for placing a head or a leg of the dialysis subject in the dialysis apparatus may be adjusted so as to suppress decrease in the regional oxygen saturation.

INDUSTRIAL APPLICABILITY

The embodiments can be used as a dialysis system and a dialysis system operation method capable of more reliably suppressing occurrence of symptoms due to cerebral blood flow reduction during hemodialysis operation.

REFERENCE SIGNS LIST

1—dialysis system, 10—dialysis apparatus, 20—measurement apparatus, 30—control apparatus, 101—anticoagulant supply unit, 102—pump, 103—pressure gauge, 104—dialyzer, 105—dialysis fluid supply unit, 106—dialysis fluid container, 107—waste fluid container, 108—replacement fluid supply unit, 109—replacement fluid supply unit, 110—pressure gauge, 111—placing stage.

The invention claimed is:

1. A dialysis system comprising:
a dialysis apparatus configured to perform hemodialysis on a dialysis subject;
a measurement apparatus configured to measure a regional oxygen saturation of the dialysis subject;
a probe connected to the measurement apparatus, provided on a forehead of the dialysis subject, and including an emission unit and a plurality of detection units which are spaced apart from each other; and
a control apparatus configured to adjust a hemodialysis operating condition by the dialysis apparatus so as to suppress decrease in the regional oxygen saturation based on the regional oxygen saturation measured by the measurement apparatus during operation of the hemodialysis by the dialysis apparatus, wherein
the measurement apparatus is configured to apply light from the emission unit to the forehead of the dialysis subject, and detect the light after being scattered and absorbed in a brain of the dialysis subject by each of the plurality of detection units,

the measurement apparatus is configured to measure, as the regional oxygen saturation, a cerebral regional oxygen saturation in each of a plurality of portions of the forehead of the dialysis subject corresponding to the plurality of detection units of the probe, and the measurement apparatus is configured to, when any measured value out of measured values of the cerebral regional oxygen saturation in the plurality of portions is determined to be abnormal, exclude the abnormal measured value and use another measured value.

2. The dialysis system according to claim 1, wherein the control apparatus is configured to adjust the hemodialysis operating condition by the dialysis apparatus so as to suppress decrease in the regional oxygen saturation when a decrease ratio of the regional oxygen saturation measured by the measurement apparatus during the operation of the hemodialysis by the dialysis apparatus becomes larger than a threshold value with respect to the regional oxygen saturation measured by the measurement apparatus before the operation of the hemodialysis by the dialysis apparatus.

3. The dialysis system according to claim 1, wherein the control apparatus is configured to adjust the hemodialysis operating condition by the dialysis apparatus so as to suppress decrease in the regional oxygen saturation when a decreasing rate of the regional oxygen saturation measured by the measurement apparatus during the operation of the hemodialysis by the dialysis apparatus becomes larger than a threshold value.

4. The dialysis system according to claim 1, wherein the control apparatus is configured to adjust a blood flow rate in the dialysis apparatus so as to suppress decrease in the regional oxygen saturation.

5. The dialysis system according to claim 1, wherein the control apparatus is configured to adjust a dialysis fluid flow rate in the dialysis apparatus so as to suppress decrease in the regional oxygen saturation.

6. The dialysis system according to claim 1, wherein the control apparatus is configured to adjust a temperature of a dialysis fluid in the dialysis apparatus so as to suppress decrease in the regional oxygen saturation.

7. The dialysis system according to claim 1, wherein the control apparatus is configured to adjust a water removal amount in the dialysis apparatus so as to suppress decrease in the regional oxygen saturation.

8. The dialysis system according to claim 1, wherein the control apparatus is configured to adjust an amount or timing of fluid replacement in the dialysis apparatus so as to suppress decrease in the regional oxygen saturation.

9. The dialysis system according to claim 1, wherein the control apparatus is configured to adjust a height of a placing stage configured to place a head or a leg of the dialysis subject in the dialysis apparatus so as to suppress decrease in the regional oxygen saturation.

* * * * *